United States Patent
Lee et al.

(10) Patent No.: US 10,376,615 B2
(45) Date of Patent: Aug. 13, 2019

(54) MICRO-NEEDLE AND MICRO-NEEDLE PATCH

(71) Applicant: SMALL LAB Co., Ltd, Daejeon (KR)

(72) Inventors: Jeong Gyu Lee, Daejeon (KR); Chang Hyeon Kim, Chungcheongnam-do (KR)

(73) Assignee: SMALL LAB Co., Ltd, Daejeon (KR)

( * ) Notice: Subject to any disclaimer, the term of this patent is extended or adjusted under 35 U.S.C. 154(b) by 0 days.

(21) Appl. No.: 14/936,825

(22) Filed: Nov. 10, 2015

(65) Prior Publication Data

US 2016/0129164 A1  May 12, 2016

(30) Foreign Application Priority Data

Nov. 10, 2014  (KR) .................. 10-2014-0155266

(51) Int. Cl.
| | | |
|---|---|---|
| A61L 31/14 | (2006.01) | |
| A61K 9/00 | (2006.01) | |
| A61M 37/00 | (2006.01) | |
| A61L 31/12 | (2006.01) | |
| A61L 31/16 | (2006.01) | |
| A61Q 19/08 | (2006.01) | |
| A61K 8/02 | (2006.01) | |
| A61K 9/14 | (2006.01) | |
| A61K 9/70 | (2006.01) | |

(52) U.S. Cl.
CPC .......... *A61L 31/146* (2013.01); *A61K 8/0279* (2013.01); *A61K 9/0021* (2013.01); *A61L 31/129* (2013.01); *A61L 31/16* (2013.01); *A61M 37/0015* (2013.01); *A61Q 19/08* (2013.01); *A61K 9/146* (2013.01); *A61K 9/7023* (2013.01); *A61K 2800/87* (2013.01); *A61K 2800/91* (2013.01); *A61L 2420/02* (2013.01); *A61M 2037/0023* (2013.01); *A61M 2037/0046* (2013.01); *A61M 2037/0053* (2013.01)

(58) Field of Classification Search
None
See application file for complete search history.

(56) References Cited

U.S. PATENT DOCUMENTS

| | | | |
|---|---|---|---|
| 8,062,573 B2* | 11/2011 | Kwon .................. | A61K 9/0021 264/319 |
| 2009/0035446 A1* | 2/2009 | Kwon .................. | A61K 9/0021 427/2.1 |

FOREIGN PATENT DOCUMENTS

JP  2013-027742  2/2013

* cited by examiner

*Primary Examiner* — Robert A Wax
*Assistant Examiner* — Melissa S Mercier

(57) ABSTRACT

Provided are micro-needles and a micro-needle patch for transdermal delivery of a pharmaceutical, medical, or cosmetic substance. The micro-needle may include a biocompatible matrix having a micro-needle-like shape; and porous particles provided at at least a portion of a surface or the interior of the biocompatible matrix.

18 Claims, 5 Drawing Sheets

MICRO-NEEDLE AND MICRO-NEEDLE PATCH

CROSS-REFERENCE TO RELATED APPLICATION

This application claims priority of Korean Patent Application No. 10-2014-0155266, filed on Nov. 10, 2014, in the KIPO (Korean Intellectual Property Office), the disclosure of which is incorporated herein entirely by reference.

BACKGROUND OF THE INVENTION

Field of the Invention

The present disclosure relates to a micro-needle, and more particularly, to a micro-needle and a micro-needle patch for transdermal delivery of active substances having pharmaceutical, medical, or cosmetic effects.

Description of the Related Art

For effective drug delivery of medicines for human body, a method of injecting a liquefied medicine via a hypodermic injection needle is widely used. However, a hypodermic injection needle having a diameter of several mm may stimulate a plurality of pain spots in a skin and induce pain to a patient, and a high skill-level is necessary to use the hypodermic injection needle.

Recently, to resolve the problems of a hypodermic injection needle, transdermal drug delivery methods using micro-needles having diameters and heights from dozens of μm to hundreds of μm are being actively researched. A micro-needle device simultaneously forms a large number of channels penetrating through an outer skin by using micro-needles for penetrating through the stratum corneum layer of a skin, which is a major barrier of transdermal drug delivery. A sufficient amount of a drug may be delivered to an epidermis layer or a dermis layer via the channels. Next, the drug are absorbed by blood vessels and lymph glands and is introduced into the circulation system of a human body.

In another example, the micro-needles are also used for cosmetic purposes. For example, a bioactive substance is applied onto a skin or micro-needles, and the bioactive substance is transdermally delivered by forming micro-channels in the skin by using the micro-needles.

Although the technique for transdermally delivering an effective substance by using the above-stated micro-needles is useful, patch-type micro-needles, which is a simplified form of a conventional micro-needle device having a complicated structure, is preferable. Furthermore, if micro-needles additionally contain a medically or cosmetically effective substance, it is necessary to secure process consistency with fabrication of micro-needles having fine structure and a mechanism for optimal application of effects and drug adjustment at a transdermal delivery.

SUMMARY OF THE INVENTION

Embodiments of the inventive concept includes a micro-needle for effective transdermal delivery of a medical or cosmetic effective substance without a high skill level or pain, where the effective substance may be applied for specialized purposes including medical or cosmetic purposes.

Embodiments of the inventive concept also include a micro-needle patch with improved user convenience by employing micro-needles having the above-stated advantages.

Embodiments of the inventive concept also include a method of fabricating the micro-needles.

According to an aspect of the inventive concept, there is provided a micro-needle including a biocompatible matrix having a micro-needle-like shape; and porous particles provided at at least a portion of a surface or the interior of the biocompatible matrix. The biocompatible matrix contains a bio-derived soluble substance, which is at least one of chitosan, collagen, gelatine, hyaluronic acid (HA), alginate, pectin, carrageenan, chondroitin (sulfate), cyclodextrin (sulfate), poly-lysine, carboxymethyl titin, fibrin, agarose, pullulan, and cellulose; a biocompatible substance, which is at least one of polyvinylpyrrolidone (PVP); Polyethylene glycol (PEG), polyvinyl alcohol (PVA), hydroxypropyl cellulose (HPC), hydroxyethyl cellulose (HEC), hydroxypropylmethylcellulose (HPMC), sodium carboxymethyl cellulose, polyvinyl alcohol, gum arabic, see Nate, cyclodextrin, dextrin, glucose, fructose, starch, trehalose, glucose, maltose, lactose, lactulose, fructose, to Lanos, Melissa Toth, Mel Reg Toth, dextran, sorbitol, xylitol, palatinit, polylactic acid (polylactic acid), polyglycolic acid (polyglycolic acid), polyethylene oxide, polyacrylic acid, polyacrylamide, polymethacrylic acid, and poly-maleic acid; a derivative of the above-stated substances; or a mixture thereof.

According to an embodiment, the biocompatible matrix contains a bio-derived soluble substance. The porous particles contain any one of poly(p-dioxanone) (PPDX), poly (lactide-co-glycolide) (PLGA), polycaprolactone, polylatic acid, polyanhydride, polyorthoester, polyetherester, polyesteramide, polybutyric acid, or a mixture thereof.

Average size of the porous particles is from about 01 μm to about 100 μm. A weight of porous fine particles against a total weight of the biocompatible matrix and the porous fine particles is from about 01 wt % to about 95 wt %.

The porous particles contain a pharmaceutical, medical, or cosmetic effective substance. The effective substance includes proteins, peptides, genes, antibodies, anesthetics, insulin, vaccines, polysaccharides, synthetic organic compounds, a synthetic inorganic compounds, or cosmetic substances.

According to an embodiment, the effective substance is trapped in pores of the porous particles, and the pores of the porous particles include open or closed pores with opening controlled to control a speed of releasing the effective substance in a living tissue. According to another embodiment, the effective substance is dispersed in matrixes of the porous particles, and the pores of the porous particles include open or closed pores with opening controlled to control a speed of releasing the effective substance in a living tissue.

According to an aspect of the inventive concept, there is provided a micro-needle patch including a substrate; and an array of the micro-needles of claim 1 formed on the substrate. According to an embodiment, the substrate and biocompatible matrixes of the array of the micro-needle are integrally formed of a same material.

According to an aspect of the inventive concept, there is provided a method of fabricating a micro-needle, the method including forming a micro-needle including a biocompatible matrix having a micro-needle-like shape; and coating a surface of the biocompatible matrix with porous particles.

According to an aspect of the inventive concept, there is provided a method of fabricating micro-needles, the method including providing a mixed solution formed by adding a biocompatible substance and porous particles to a solvent; applying the mixed solution to a mold having an array of cavities for forming micro-needles; forming micro-needles, in which the porous particles are dispersed in matrixes formed of the biocompatible substance, by drying the mixed solution in the mold; and separating the micro-needles from the mold.

BRIEF DESCRIPTION OF THE DRAWINGS

The above and other features and advantages will become more apparent to those of ordinary skill in the art by describing in detail exemplary embodiments with reference to the attached drawings, in which.

In the following description, the same or similar elements are labeled with the same or similar reference numbers.

DETAILED DESCRIPTION

The present invention now will be described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "includes", "comprises" and/or "comprising," when used in this specification, specify the presence of stated features, integers, steps, operations, elements, and/or components, but do not preclude the presence or addition of one or more other features, integers, steps, operations, elements, components, and/or groups thereof. In addition, a term such as a "unit", a "module", a "block" or like, when used in the specification, represents a unit that processes at least one function or operation, and the unit or the like may be implemented by hardware or software or a combination of hardware and software.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Preferred embodiments will now be described more fully hereinafter with reference to the accompanying drawings. However, they may be embodied in different forms and should not be construed as limited to the embodiments set forth herein. Rather, these embodiments are provided so that this disclosure will be thorough and complete, and will fully convey the scope of the disclosure to those skilled in the art.

Figure 1A:
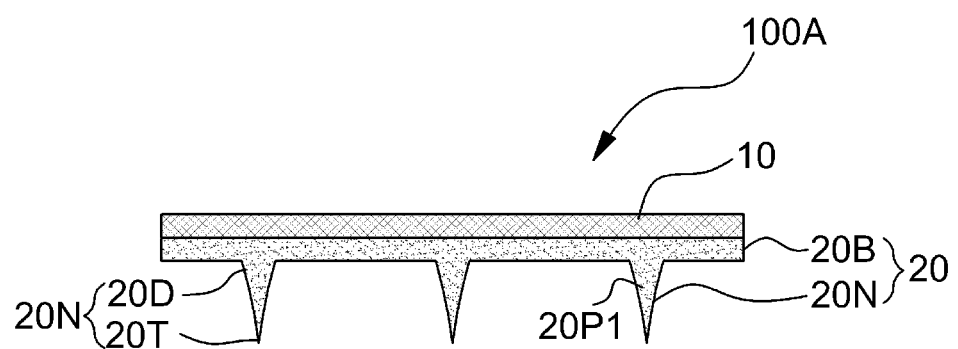
FIGS. 1A and 1B are sectional view diagrams showing structures of micro-needles according to embodiments of the present invention.
Figure 1B:
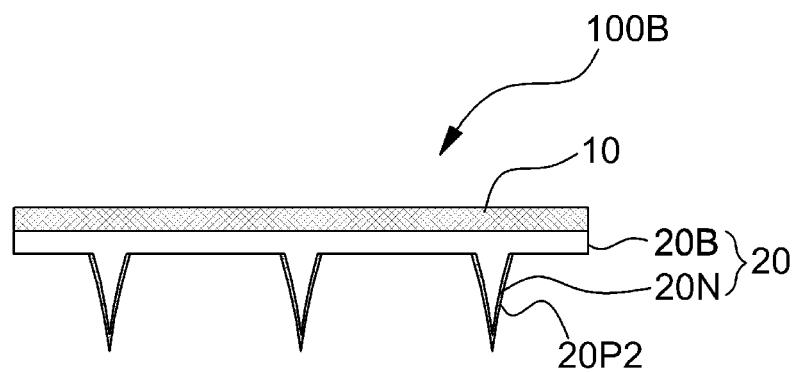

FIGS. 1A and 1B are sectional view diagrams showing structures of micro-needles 20 according to embodiments of the present invention.

Referring to FIG. 1A, micro-needles 20 include a biocompatible matrix 20N having a shape of a micro-needle.

The biocompatible matrix 20N includes an acute portion 20T that may penetrate through a skin and a base unit 20D supporting the same. As unlimited examples, height of the biocompatible matrix 20N may be from about 50 μm to about 1,500 μm, and diameter of the base unit 20D of the biocompatible matrix 20N may be from about 10 μm to about 1,000 μm.

According to an embodiment, the micro-needles 20 may further include a common base layer 20B to which the base units 20D of the plurality of biocompatible matrixes 20N are connected. According to an embodiment, the common base layer 20B and the biocompatible matrixes 20N may be integrally formed of a same biocompatible substance The biocompatible matrix 20N is formed of a biocompatible substance for minimizing side effects when the biocompatible matrix 20N penetrates through a skin and effectively delivering a drug. The biocompatible substance may swell or may be absorbed by a living tissue within from a few seconds to a few hours when the biocompatible substance penetrates through a skin. For example, the biocompatible substance may be a bio-derived soluble substance, which is at least one of chitosan, collagen, gelatine, hyaluronic acid (HA), alginate, pectin, carrageenan, chondroitin (sulfate), cyclodextrin (sulfate), poly-lysine, carboxymethyl titin, fibrin, agarose, pullulan, and cellulose; a biocompatible substance, which is at least one of polyvinylpyrrolidone (PVP); Polyethylene glycol (PEG), polyvinyl alcohol (PVA), hydroxypropyl cellulose (HPC), hydroxyethyl cellulose (HEC), hydroxypropylmethylcellulose (HPMC), sodium carboxymethyl cellulose, polyvinyl alcohol, gum arabic, see Nate, cyclodextrin, dextrin, glucose, fructose, starch, trehalose, glucose, maltose, lactose, lactulose, fructose, to Lanos, Melissa Toth, Mel Reg Toth, dextran, sorbitol, xylitol, palatinit, polylactic acid (polylactic acid), polyglycolic acid (polyglycolic acid), polyethylene oxide, polyacrylic acid, polyacrylamide, polymethacrylic acid, and poly-maleic acid; a derivative of the above-stated substances; or a mixture thereof. Preferably, the biocompatible substance may be a substance bio-degraded or dissolved in a living tissue when the biocompatible substance penetrates through a skin; e.g., at least one of chitosan, collagen, gelatine, hyaluron acid (HA), alginate, pectin, carrageenan, chondroitin (sulfate), dextrin (sulfate), poly-lysine, carboxymethyl titin, fibrin, agarose, pullulan, and cellulose.

According to some embodiments, a substrate (or liner) 10 for supporting the biocompatible matrix 20N may be provided at the micro-needles 20. The liner 10 may provide mechanical strength to an array of the micro-needles 20 and may be rigid or flexible. If necessary, another second substrate may be further provided. The liner 10 may further include penetration holes, where an additional drug delivery may be made from a side opposite to the micro-needles 20 toward a skin via the penetration holes.

According to an embodiment, the liner 10 may be a plate-like structure having a certain thickness and may be a film or a sheet structure formed of a resin-based material. As unlimited examples, the resin-based material may be polyethylene, polypropylene, polyvinyl chloride, polyethylene terephthalate (PET), nylon, epoxy, polyimide, polyester, polyurethane, acrylic, polycarbonate, urea, melamine, chlorinated rubber, polyvinyl alcohol, polyvinyl ester, polyvinyl fluoride-hexafluoropropylene copolymer (PVDF-co-HFP), polyvinylidenefluoride (PVDF), polyacrylonitrile, polymethylmethacrylate, polytetrafluoroethylene (PTFE), styrenebutadiene rubber (SBR), or ethylene-propylene-diene copolymer (EPDM). In another example, the liner 10 may be a fabric sheet having a woven structure or a non-woven structure, where the fabric sheet may be formed of any one of the above-stated resin-based materials. The above-stated resin-based materials are merely examples, and various other hardening or plastic resin-based materials may be applied.

According to another embodiment, the liner 10 may include a metal layer or a woven or non-woven sheet formed of metal fibers. The metal layer or the woven or non-woven sheet formed of metal fibers may contain aluminum, gold, silver, copper, titanium, or manganese, for example. According to another embodiment, the liner 10 may be a composite layer containing the above-stated materials, e.g., a resin-based film coated with a metal layer. Furthermore, the liner 10 is not limited to a continuous layer and may be metal nano-particles coated onto the resin-based film.

According to some embodiments, the liner 10 may have a ventilation structure, such as penetration holes or air holes. The ventilation structure is advantageous for production yield and size expansion of the biocompatible matrix 20N. Detailed descriptions thereof will be given below with reference to FIGS. 6A and 6B.

Porous particles 20P1 are provided at at least a portion of the interior of the biocompatible matrix 20N. Average size of the porous particles 20P1 is from about 0.01 μm to about 100 μm and may be from about 1 μm to about 50 μm. A weight of porous fine particles against a total weight of the biocompatible matrix and the porous fine particles may be from about 0.01 wt % to about 95 wt %.

FIG. 1A shows that the porous particles 20P1 are provided not only inside the biocompatible matrix 20N, but also inside the common base layer 20B. according to another embodiment, porous particles P may be provided only at the acute portion 20T of the biocompatible matrix 20N or a leading end region of the biocompatible matrix 20N including the acute portion 20T. According to another embodiment, the porous particles P may be distributed only in the biocompatible matrix 20N excluding the common base layer 20B.

Referring to FIG. 1B, porous particles 20P2 may be provided on a surface of the biocompatible matrix 20N. For example, the porous particles 20P2 may be coated onto a surface of the biocompatible matrix 20N as a layer. The porous particles 20P2 may be coated onto a surface of the biocompatible matrix 20N via physical absorption or adhesion, chemical absorption or adhesion, a biocompatible binder, or mechanical burial. However, the present invention is not limited thereto. For example, the porous particles 20P2 may be coated onto the biocompatible matrix 20N via deep coating or spray coating.

When the biocompatible matrix 20N penetrates through a skin and swells or is dissolved into a living tissue, the porous particles 20P1 and 20P2 are also injected into the living tissue. According to an embodiment, the porous particles 20P1 and 20P2 may be particles that cause pharmaceutical, medical, or cosmetic effects in a living tissue. The porous particles 20P1 and 20P2 may have open or closed pores as described below, where the pores may cause effective pharmaceutical, medical, or cosmetic effects due to increased surface areas.

According to an embodiment, the porous particles 20P1 and 20P2 may be fillers having a cosmetic effect for removing wrinkles. The fillers in the form of porous particles contact living tissues at increased area due to increased surface areas based on pores at surfaces of the porous particles 20P1 and 20P2, thereby stimulating generation of collagen attached thereto more efficiently. As a result, wrinkles may be quickly removed, and, due to increased roughness of surfaces of the fillers, the fillers may be fixed in the living tissues more firmly.

Furthermore, due to a reduced weight to volume, the fillers in the form of porous particles may minimize irritation when applied to a living body and be mechanically flexible and soft. Even if the porous particles 20P1 and 20P2 have closed pores, if the porous particles 20P1 and 20P2 are formed of a bio-degradable or bio-soluble substance, the porous particles 20P1 and 20P2 are gradually degraded in a living tissue and the closed pores are sequentially opened. As a result, the above-stated effects of the pores may be secured.

The fillers in the form of porous particles may contain poly(p-dioxanone) (PPDX), poly(lactide-co-glycolide) (PLGA), polycaprolactone, polylatic acid, polyanhydride, polyorthoester, polyetherester, polyesteramide, polybutyric acid, or a mixture of two or more thereof. The above-stated substances are merely examples, and the fillers in the form of porous particles may contain various other biocompatible substances.

In case of performing a cosmetic procedure by combining fillers in the form of porous particles with micro-needles, unlike a conventional procedure using an syringe for paralyzing wrinkle-causing muscles with the Botox, the procedure does not cause an unnatural face and may be easily applied to regions at which it is difficult to performing a cosmetic procedure using a syringe, e.g., regions below eyes, a lower lip, and a nasolabial folds. Furthermore, by controlling solubility of porous particles in a living tissue, effects thereof may be maintained over a year or permanently. Furthermore, compared to a technique for directly injecting gold threads or thread-like fillers formed of other biocompatible substances into a skin by using a syringe in the related art, micro-needles containing fillers according to an embodiment of the present invention causes no pain, does not require an additional process like a general anesthesia, and does not require a medical surgeon to be highly skilled.

The porous particles 20P1 and 20P2 may be applied as both the fillers as described above and drug carriers at the same time may be applied as drug carriers independently. For example, the porous particles 20P1 and 20P2 may additionally contain pharmaceutically, medically, or cosmetically effective substance therein, and thus the porous particles and the effective substance may be simultaneously delivered to a living tissue when micro-needles penetrate through a skin. As unlimited examples, the effective substance may be one of cosmetic substances, such as proteins, peptides, genes, antibodies, anesthetics, insulin, vaccines, polysaccharides, synthetic organic compounds, synthetic inorganic compounds, whitening agents, or antioxidants, or any of various other effective substances that are allowed to be used for pharmaceutical, medical, or cosmetic purposes. The effective substances may be trapped inside pores of the porous particles 20P1 and 20P2 or distributed in the matrixes of the porous particles 20P1 and 20P2 and delivered to a living tissue. Detailed descriptions thereof will be given below.

Porosity of the porous particles may be from 5% to 90%, for example. The porosity may be suitably selected based on an amount of cosmetically or pharmaceutically effective substance to be loaded. Furthermore, in case of using porous particles as fillers, porosity of the porous particles may be suitably selected to adjust filling effect that the porous particles are combined with a living tissue and regenerates the living tissue.

Figure 2A:
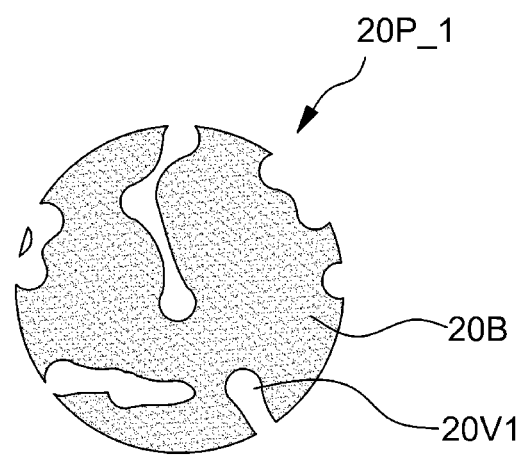
FIGS. 2A and 2B are sectional view diagrams showing porous structures of porous particles according to various embodiments of the present invention.
Figure 2B:
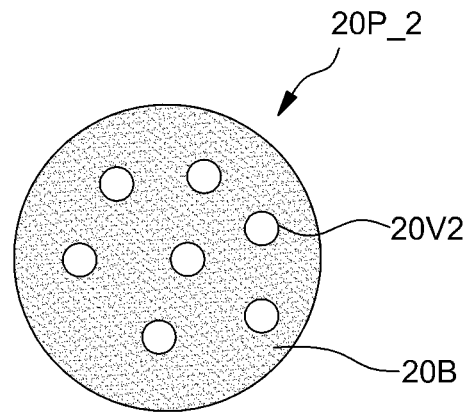

FIGS. 2A and 2B are sectional view diagrams showing porous structures of the porous particles 20P_1 and 20P_2 according to various embodiments of the present invention.

Referring to FIG. 2A, the porous particles 20P_1 may have an open pore 20V1 having an opening at a surface of the common base layer 20B constituting a particle body. According to another embodiment, the porous particles 20P_2 may have a closed pore 20V2 formed inside the common base layer 20B. According to another embodiment, a porous particle may include both the open pore 20V1 and the closed pore 20V2.

To form the porous particles 20P_1 and 20P_2, a mixed solution is prepared by dissolving a biocompatible substance constituting the common base layer 20B (preferably, a bio-degradable polymer substance) and an amphiphile polymer, which may be dissolved in an aqueous solution, in an organic solvent. As unlimited examples, the biocompatible substance may be a bio-degradable polymer, such as poly (p-dioxanone) (PPDX), poly(lactide-co-glycolide) (PLGA), polycaprolactone, polylatic acid, polyanhydride, polyorthoester, polyetherester, polyesteramide, polybutyric acid, or a mixture of two or more thereof.

As an unlimited example, the amphiphile polymer may be pluronic (more particularly, Pluronic F127 ((PEG)99(PPG)69(PEG)99) sold by BASF in Korea). A ratio of weight $W_p$ of the amphiphile polymer to the total weight $W_{total}$ of the bio-degradable polymer substance and the amphiphile polymer is from 5 wt % to 95 wt % and may be from 15 wt % to 80 wt %. Size and porosity of a pore may be controlled based on the ratio $W_p/W_{total}$. The organic solvent may be dichloromethane, chloroform, or methylene chloride. Porosity may be determined based on an amount of the amphiphile polymer.

The mixed solution is added to an aqueous solution having dissolved therein an emulsifying agent, thereby forming an emulsion solution. As an unlimited example, the emulsifying agent may be polyvinyl alcohol (88% hydrolyzed, MW 13,000-23,000). For example, the polyvinyl alcohol may be added to the aqueous solution at the concentration of 0.5%. The emulsion solution is dispersed at a high speed by using a mixer, thereby evaporating the organic solvent. Here, as the organic solvent is evaporated, pores are formed in the matrix, and thus porous particles are extracted.

As a ratio of the amphiphile polymer to a biocompatible polymer substance constituting the common base layer 20B of the porous particles 20P_1 increases, size of the porous particles (20P_1) may increase, and size of pores on a surface thereof may also increase. Since a relative volume of a hydrophilic amphiphile polymer increases in an emulsion droplet, a larger domain is formed in the matrix as the amphiphile polymer is diffused to outside, and more moisture is introduced into the domain. As a result, a large pore is formed when the moisture is evaporated.

Next, the porous particles 20P_1 are obtained in a separating operation and/or a filtering operation, such as a centrifugation or filtering. If necessary, an operation for washing the obtained porous particles 20P_1 may be performed, and solid fine porous particles may be provided via a lyophilisation. Porous particles fabricated as described above feature a reduced weight to volume ratio regarding materials constituting the same, thereby increasing a number of particles or a volume of particles per unit weight of a polymer used therein. Therefore, porous particles may be fabricated more inexpensively as compared to non-porous particles.

Figure 3A:
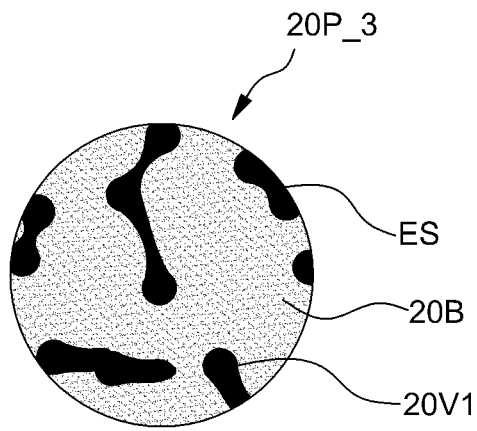
FIGS. 3A and 3B are sectional view diagrams showing porous particles containing an effective substance according to various embodiments of the present invention.
Figure 3B:
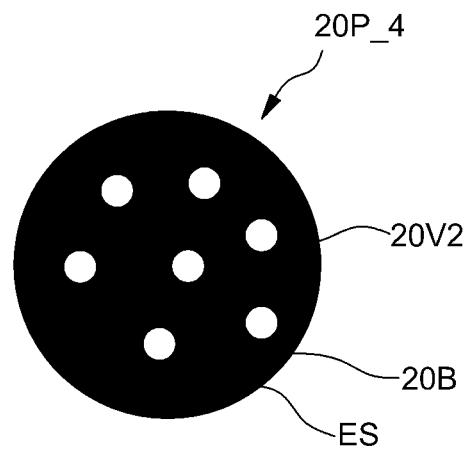

FIGS. 3A and 3B are sectional view diagrams showing porous particles 20P_3 and 20P_4 containing an effective substance ES according to various embodiments of the present invention.

Referring to FIG. 3A, a porous particle 20P_3 may contain a pharmaceutically, medically, or cosmetically effective substance ES trapped inside the pore 20V1. The pore 20V1 may be a closed pore. The effective substance ES may be trapped inside the pore 20V1 of the porous particle 20P_3 by adding fabricated porous particles, e.g., porous particles having open pores, to a buffer solution having dissolved therein the effective substance ES and mixing the same for a certain time period. As a result, the porous particle 20P_3 in which the effective substance ES is introduced into the open pores may be fabricated.

Next, to close the open pores of the porous particle 20P_3 containing the effective substance ES, the suspended aqueous solution having dispersed therein the porous particles may be heated to a temperature nearby the softening point temperature of a bio-degradable polymer substance constituting a matrix 20B of the porous particles. Alternatively, a pore closing solvent, such as ethanol, acetic nitrile, or tetrahydrofuran, may be added to the suspended aqueous solution and mixed. As a result, surfaces of the porous particles may be closed. If the effective substance ES is trapped inside the porous particle 20P_3, when micro-needles penetrate through a skin, the porous particle 20P_3 is delivered into a living tissue and gradually degraded thereat to release the effective substance ES therein, where a speed of releasing the effective substance ES may be controlled. According to another embodiment, after the effective substance ES is trapped in open pores of the porous particle 20P_3, the porous particle 20P_3 may be applied directly to micro-needles without closing the open pores.

Referring to FIG. 3B, a porous particle 20P_4 may contain the effective substance ES inside the matrix 20B. The structure may be obtained by fabricating the porous particle 20P_4 by adding the effective substance ES to a mixture solution during fabrication of the porous particle 20P_4.

As described above, according to an embodiment of the present invention,

By adding not only an effective substance having a cosmetic effect of wrinkle enhancement, but also other effective substances having pharmaceutical or medical effects in pores and/or matrixes of porous particles and delivering the effective substances to a living tissue via micro-needles, substances that may be limitedly used due to potential instabilities, such as proteins, peptides, genes, or anti-oxidants, may be included in porous particles to have high stability, and release of the effective substance may be controlled by delivering the porous particles containing the effective substance. The effect of the present invention may not be embodied by using non-porous particles. Furthermore, according to an embodiment of the present invention, an effective substance is contained in porous particles, and a speed of releasing the effective substance may be controlled by controlling porosity, size of pores and/or opening of the pores. Particularly, degradation of porous particles formed of a bio-degradable polymer may be controlled to be faster or slower than degradation of non-porous particles. Based on the property, porous particles may be designed to maintain shapes for a desired time period by controlling porosity, thereby controlling a speed of releasing a contained effective substance.

Hereinafter, experimental embodiments of fabrication of porous particles and micro-needles according to an embodiment of the present invention will be described in detail. However, the below experimental embodiments are merely examples, and embodiments of the present invention should not be limited thereto.

First Embodiment: Fabrication of Porous Particles

A mixed solution is formed by dissolving 0.7 g of poly(lactide-co-glycolide) (PLGA), which is a bio-degradable polymer for forming matrixes of porous particles, and 0.3 g of Pluronic F127 g in 3 ml of dichloromethane, which is a solvent. The mixed solution is added to a 100 ml of distilled water in which 0.5 wt % of polyvinyl alcohol (MW 13,000-23,000) and is mixed at a high speed by using a homogenizer for 90 seconds.

Next, while slowing mixing the same by using a magnetic mixer, the dichloromethane is removed by evaporating the same for 4 hours at the room temperature, and porous particles having PLGA matrixes are obtained by using a centrifugal separator. While the solvent is being evaporated, water-soluble F127 is diffused to outside and forms pores. By sufficiently removing the dichloromethane, porous particles having water-filled pores are formed. Next, the porous particles are washed three times by using distilled water and moisture is completed removed therefrom via lyophilisation. As a result, fine porous particles are obtained.

Figure 4A:
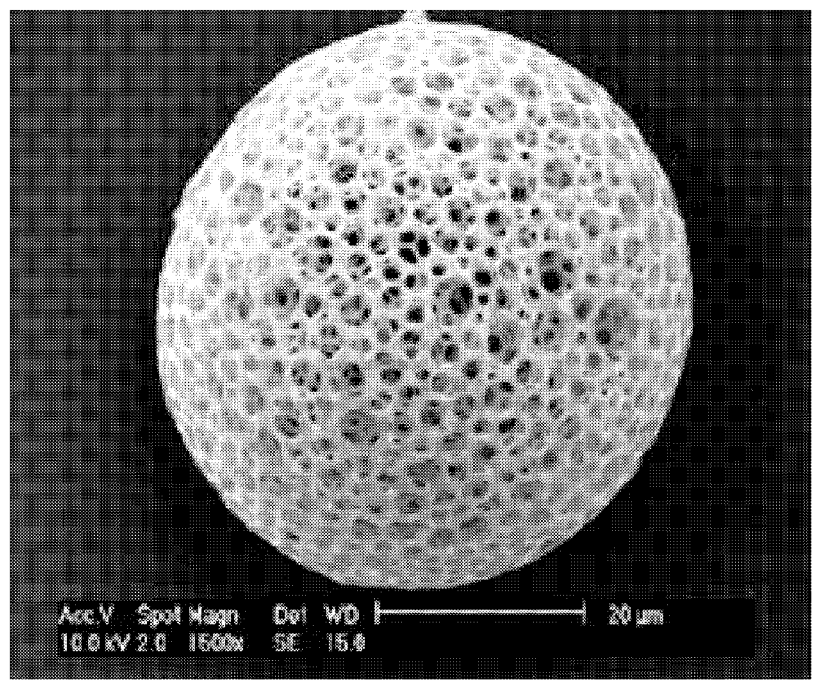
FIGS. 4A and 4B are scan electron microscope images of a surface and a section of a porous particle having open pores.
Figure 4B:
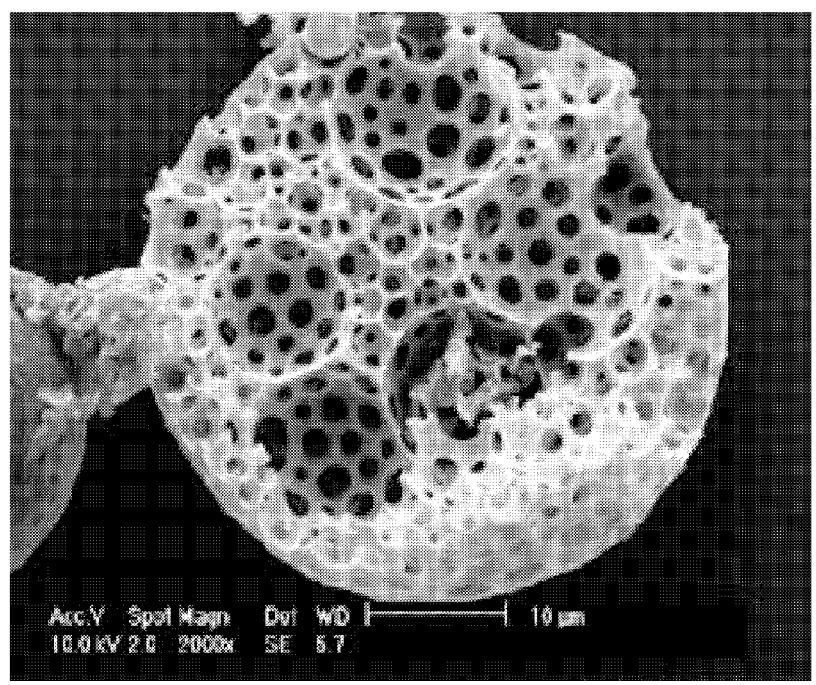
Figure 5A:
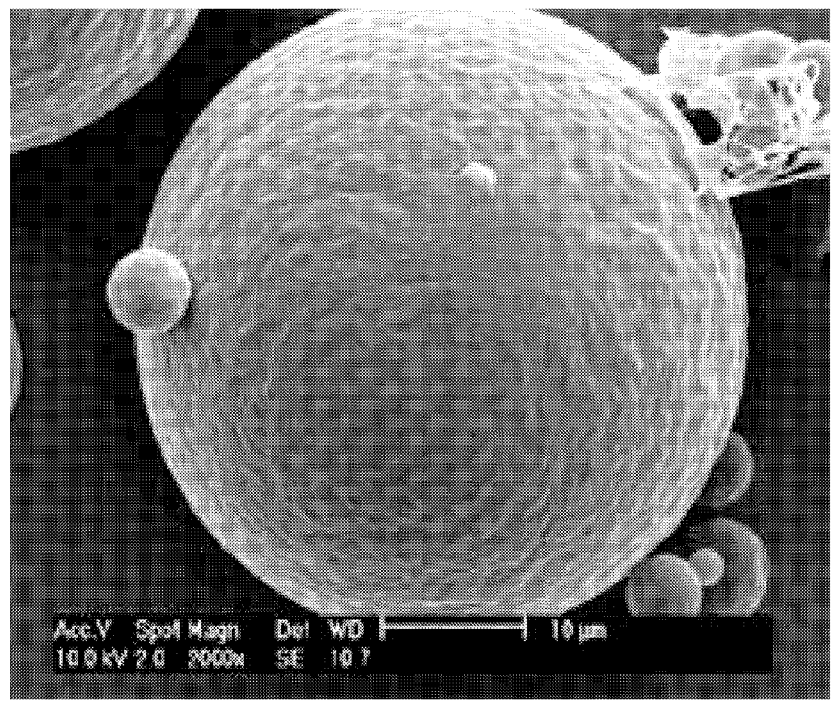
FIGS. 5a and 5B are scan electron microscope images of a surface and a section of a porous particle having closed pores.
Figure 5B:
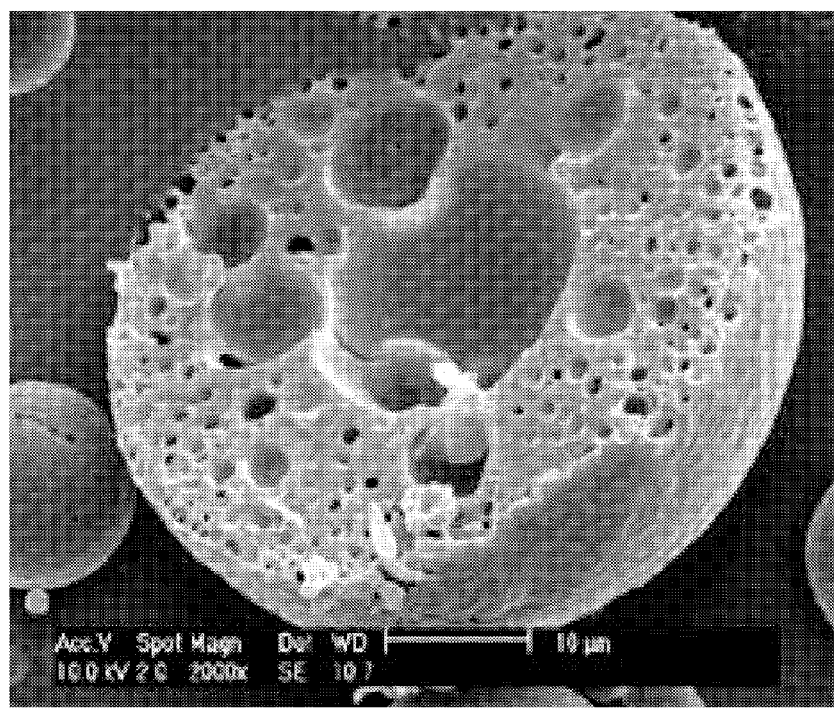

The obtained porous particles have open pores as shown in scan electron microscope images of a surface and a section shown in FIGS. 4A and 4B. Next, ethanol is added to an aqueous solution having dispersed therein the obtained porous particles as a pore closing solvent for closing the pores, thereby softening surfaces of the porous particles. As a result, the pores are closed. Scan electron microscope images of a surface and a section of porous particles with closed pores are shown in FIGS. 5A and 5B, respectively.

Figure 6A:
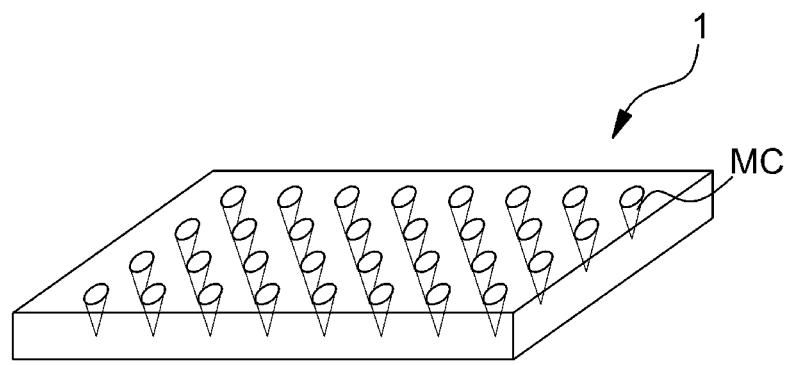
FIG. 6a is a perspective view of a mold having an array of cavities for forming micro-needles.
Figure 6B:
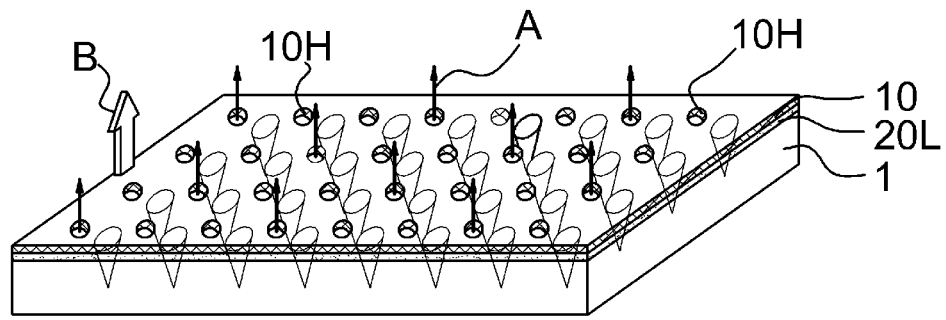
FIG. 6B is a perspective view diagram for describing a method of fabricating micro-needles.

Second Embodiment: Fabrication of Micro-Needle Patch Containing Fine Porous Particles for Enhancing Wrinkles A mixed solution was formed by mixing 0.5 g of the porous particles fabricated in the first embodiment with 10 g of hyaluronic acid, which is a biocompatible substance, and adding the mixture to 500 ml of distilled water. The mixed solution was applied to a mold having an array of cavities MC for forming the micro-needles as shown in FIG. 6A. Thickness of a common base layer of a micro-needle patch for wrinkle enhancement is from about 250 μm to about 350 μm. In consideration of the same, as shown in FIG. 6B, the mixed solution 20L is applied to the mold 1. The distilled water is merely an example. According to another embodiment, solvent of the mixed solution may be deionized water or a suitable hydrophilic or lyphophilic polar solvent that is a good solvent for a biocompatible substance constituting a matrix of a micro-needle and is a poor solvent for porous particles.

Next, the mixed solution in the mold 1 is dried at the room temperature (e.g., 25° C.) or a high temperature (e.g., a temperature from 50° C. to 100° C.). In the experiment, the mixed solution was dried at 50° C. for 2 hours. Next, dried micro-needles were separated from the mold 1. In the above-stated method, a ratio of a weight of porous particles to the total weight of the matrix of the micro-needle and the porous particles may be within a range from 0.01 wt % to 95 wt %

According to an embodiment, a liner 10 may be stacked on the applied mixed solution 20L before being dried. The liner 10 may have penetration holes 10H. The penetration holes 10H may help draining of moisture from the mixed solution 20L being dried. Next, as indicated by the arrow B, the dried micro-needle layer was separated from the mold 1, and thus micro-needles containing porous particles were fabricated.

According to another embodiment, after micro-needles are fabricated according to the above-stated method, a solution having dispersed therein porous particles may be coated onto the micro-needles, and thus a micro-needle patch containing the porous particles may be fabricated. Application of porous particles may be performed via deep coating or spray coating.

Figure 7:
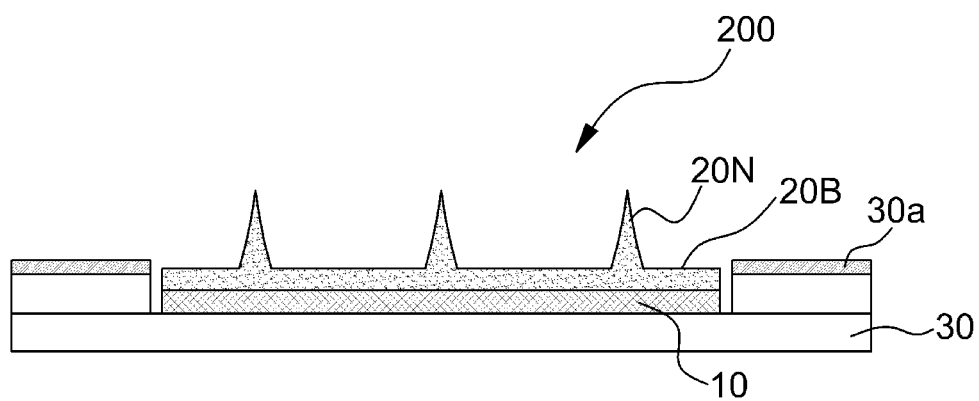
FIG. 7 is a sectional view of a micro-needle patch according to an embodiment of the present invention.

Next, as shown in FIG. 7, micro-needles may be manufactured in the form of a micro-needle patch 200. The micro-needle patch 200 is cut and molded to have a size and a shape to be stably attached to regions including regions below eyes, regions around a mouth, arm regions, shoulder regions, and abdomen regions and includes an adhesive layer 30a to stably maintain attachment of the same to a skin. The adhesive layer 30a may be fabricated by attaching an attachment pad 30 providing the adhesive layer 30a, which expands over edges of the micro-needle patch 200 for skin attachment, onto the bottom surface of the liner 10. The attachment pad 30 and the liner 10 may be combined with each other via an adhesive layer arranged therebetween.

According to an embodiment of the present invention, porous particles having pharmaceutical, medical, or cosmetic effects may be transdermally delivered into a living tissue by simply adhering the micro-needle patch 200 to a desired location without a high skill level. Furthermore, a degrading speed may be controlled to be faster or slower by controlling degradability in a living tissue. Therefore, based on the property, porous particles may be designed to maintain shapes for a desired time period by controlling porosity, and thus a speed of releasing an effective substance contained in the porous particles may be controlled.

According to an embodiment of the present invention, there is provided micro-needles that, since porous particles are provided at at least a portion of a surface or the interior of a micro-needle type biocompatible matrix, may deliver the porous particles into a living tissue simply by penetrating through a skin without requiring high skill level or causing pain, may optimize pharmaceutical, medical, or cosmetic effects of the porous particles with increased surface areas of the porous particles, and may stably deliver an effective substance contained in pores and/or matrixes of the porous particles into a living tissue or control a speed of releasing the effective substance.

Furthermore, according to an embodiment, an easy-to-use micro-needle patch having the above-stated advantages may be provided.

While the present disclosure has been described with reference to the embodiments illustrated in the figures, the embodiments are merely examples, and it will be understood by those skilled in the art that various changes in form and other embodiments equivalent thereto can be performed. Therefore, the technical scope of the disclosure is defined by the technical idea of the appended claims The drawings and the forgoing description gave examples of the present invention.

The scope of the present invention, however, is by no means limited by these specific examples. Numerous variations, whether explicitly given in the specification or not, such as differences in structure, dimension, and use of material, are possible. The scope of the invention is at least as broad as given by the following claims.

What is claimed is:

1. A micro-needle comprising:
a biocompatible matrix having a micro-needle-like shape and having a first material configured to be swollen or dissolved in a living tissue; and
particles provided at at least a portion of a surface or an interior of the biocompatible matrix,
wherein the particles have a particle body and a plurality of pores formed therein,
wherein the particle body comprises a second material different from the first material,
wherein the particles function as drug carriers containing pharmaceutically, medically, or cosmetically effective substance for delivering the pharmaceutically, medically, or cosmetically effective substance to the living tissue,
wherein the effective substance is trapped in the plurality of pores of the particles,
wherein the plurality of pores of the particles comprise open or closed pores, and at least one of porosity, size and opening of the open or closed pores is controlled to control a speed of releasing the effective substance in the living tissue,
wherein the porosity of the particles has a range from 5% to 90%.

2. The micro-needle of claim 1, wherein the biocompatible matrix contains a bio-derived soluble substance, which is at least one of chitosan, collagen, gelatine, hyaluronic acid (HA), alginate, pectin, carrageenan, chondroitin (sulfate), cyclodextrin (sulfate), poly-lysine, carboxymethyl titin, fibrin, agarose, pullulan, and cellulose; a biocompatible substance, which is at least one of polyvinylpyrrolidone (PVP); Polyethylene glycol (PEG), polyvinyl alcohol (PVA), hydroxypropyl cellulose (HPC), hydroxyethyl cellulose (HEC), hydroxypropylmethylcellulose (HPMC), sodium carboxymethyl cellulose, polyvinyl alcohol, gum arabic, cyclodextrin, dextrin, glucose, fructose, starch, trehalose, maltose, lactose, lactulose, turanose, melitose, melezitose, dextran, sorbitol, xylitol, polylactic acid, polyglycolic acid, polyethylene oxide, polyacrylic acid, polyacrylamide, polymethacrylic acid, and poly-maleic acid; a derivative of the above-stated substances; or a mixture thereof.

3. The micro-needle of claim 1, wherein the biocompatible matrix contains a bio-derived soluble substance.

4. The micro-needle of claim 1, wherein the particles contain any one of poly(p-dioxanone) (PPDX), poly(lactide-co-glycolide) (PLGA), polycaprolactone, polylatic acid, polyanhydride, polyorthoester, polyetherester, polyesteramide, polybutyric acid, or a mixture thereof.

5. The micro-needle of claim 1, wherein the particles are fillers for removing wrinkles.

6. The micro-needle of claim 1, wherein average size of the particles is from about 0.01 μm to about 100 μm.

7. The micro-needle of claim 1, wherein a weight of porous fine particles against a total weight of the biocompatible matrix and the porous fine particles is from about 0.01 wt % to about 95 wt %.

8. The micro-needle of claim 1, wherein the effective substance comprises proteins, peptides, genes, antibodies, anesthetics, insulin, vaccines, polysaccharides, synthetic organic compounds, a synthetic inorganic compounds, or cosmetic substances.

9. A micro-needle comprising:
a biocompatible matrix having a micro-needle-like shape and having a first material configured to be swollen or dissolved in a living tissue; and
particles provided at at least a portion of a surface or an interior of the biocompatible matrix,
wherein the particles have a particle body and a plurality of pores formed therein,
wherein the particle body comprises a second material different from the first material,
wherein the particles function as drug carriers containing pharmaceutically, medically, or cosmetically effective substance for delivering the pharmaceutically, medically, or cosmetically effective substance,
wherein the effective substance is dispersed in matrixes of the particles, and the pores of the particles comprise open or closed pores with opening controlled to control a speed of releasing the effective substance in the living tissue,
wherein the porosity of the particles has a range from 5% to 90%.

10. A micro-needle comprising:
a biocompatible matrix containing a bio-derived soluble substance and having a first material configured to be swollen or dissolved in a living tissue; and
particles provided at a portion of a surface of the biocompatible matrix,
wherein average size of the particles is from about 0.01 μm to about 100 μm,
wherein the particles have a particle body and a plurality of pores formed therein,
wherein the particle body comprises a second material different from the first material,
wherein the particles function as drug carriers containing pharmaceutically, medically, or cosmetically effective substance for delivering the pharmaceutically, medically, or cosmetically effective substance,
wherein the effective substance is trapped in the plurality of pores of the particles,
wherein the plurality of pores of the particles comprise open or closed pores, and at least one of porosity, size and opening of the open or closed pores is controlled to control a speed of releasing the effective substance,
wherein the porosity of the particles has a range from 5% to 90%.

11. The micro-needle of claim 10, wherein the bio-derived soluble substance is at least one of chitosan, collagen, gelatine, hyaluronic acid (HA), alginate, pectin, carrageenan, chondroitin (sulfate), cyclodextrin (sulfate), poly-lysine, carboxymethyl titin, fibrin, agarose, pullulan, and cellulose; a biocompatible substance, which is at least one of polyvinylpyrrolidone (PVP); Polyethylene glycol (PEG), polyvinyl alcohol (PVA), hydroxypropyl cellulose (HPC), hydroxyethyl cellulose (HEC), hydroxypropylmethylcellulose (HPMC), sodium carboxymethyl cellulose, polyvinyl alcohol, gum arabic, cyclodextrin, dextrin, glucose, fructose, starch, trehalose, maltose, lactose, lactulose, turanose, melitose, melezitose, dextran, sorbitol, xylitol, polylactic acid, polyglycolic acid, polyethylene oxide, polyacrylic acid, polyacrylamide, polymethacrylic acid, and poly-maleic acid; a derivative of the above-stated substances; or a mixture thereof.

12. The micro-needle of claim 10, wherein the particles contain any one of poly(p-dioxanone) (PPDX), poly(lactideco-glycolide) (PLGA), polycaprolactone, polylatic acid, polyanhydride, polyorthoester, polyetherester, polyesteramide, polybutyric acid, or a mixture thereof.

13. The micro-needle of claim 10, wherein the particles are fillers for removing wrinkles.

14. The micro-needle of claim 10, wherein a weight of porous fine particles against a total weight of the biocompatible matrix and the porous fine particles is from about 0.01 wt % to about 95 wt %.

15. The micro-needle of claim 10, wherein the particles contain a pharmaceutical, medical, or cosmetic effective substance.

16. The micro-needle of claim 15, wherein the effective substance comprises proteins, peptides, genes, antibodies, anesthetics, insulin, vaccines, polysaccharides, synthetic organic compounds, a synthetic inorganic compounds, or cosmetic substances.

17. The micro-needle of claim 15, wherein the effective substance is trapped in pores of the particles, and the pores of the particles comprise open or closed pores with opening controlled to control a speed of releasing the effective substance in a living tissue.

18. The micro-needle of claim 15, wherein the effective substance is dispersed in matrixes of the particles, and the pores of the particles comprise open or closed pores with opening controlled to control a speed of releasing the effective substance in a living tissue.

* * * * *